US012709066B2

(12) United States Patent
Baumann

(10) Patent No.: US 12,709,066 B2
(45) Date of Patent: Aug. 18, 2026

(54) APPARATUS, SYSTEM AND METHOD FOR GENERATING A 3D STRUCTURE

(71) Applicant: uppollux GmbH & Co. KG, Tuttlingen (DE)

(72) Inventor: Daniel Baumann, Tuttlingen (DE)

(73) Assignee: uppolluX GmbH & Co. KG, Tuttlingen (DE)

(*) Notice: Subject to any disclaimer, the term of this patent is extended or adjusted under 35 U.S.C. 154(b) by 196 days.

(21) Appl. No.: 18/519,069

(22) Filed: Nov. 26, 2023

(65) Prior Publication Data

US 2024/0092026 A1 Mar. 21, 2024

Related U.S. Application Data

(63) Continuation of application No. PCT/EP2022/064272, filed on May 25, 2022.

(30) Foreign Application Priority Data

May 26, 2021 (EP) .................................... 21176035

(51) Int. Cl.
*B29C 64/386* (2017.01)
*A61B 17/00* (2006.01)
(Continued)

(52) U.S. Cl.
CPC ...... *B29C 64/386* (2017.08); *A61B 17/00234* (2013.01); *B29C 64/165* (2017.08);
(Continued)

(58) Field of Classification Search
CPC ... B29C 64/386; B29C 64/165; B29C 64/135; B29C 64/393; A61B 17/00234;
(Continued)

(56) References Cited

U.S. PATENT DOCUMENTS

| | | | |
|---|---|---|---|
| 4,938,763 | A | 7/1990 | Dunn et al. |
| 5,411,730 | A | 5/1995 | Kirpotin et al. |

(Continued)

FOREIGN PATENT DOCUMENTS

| | | | |
|---|---|---|---|
| CN | 109 605 742 | A | 4/2019 |
| DE | 689 27 956 | T2 | 7/1997 |

(Continued)

OTHER PUBLICATIONS

Chandrasekharan et al., "Using Magnetic Particle Imaging Systems to Localize and Guide Magnetic Hyperthermia Treatment: Tracers, Hardware, and Future Medical Applications", Theranostics 2020, vol. 10, Issue 7, 2965-2981, doi: 10.7150/thno.40858.

(Continued)

*Primary Examiner* — Inja Song

(74) *Attorney, Agent, or Firm* — Orbit IP, LLP; Marc G. Martino

(57) ABSTRACT

An apparatus for generating a 3D structure is disclosed. A magnetic field generator generates a static magnetic field $B_0$ in a working zone of the apparatus, in which a polymer precursor having at least one paramagnetic substance can be arranged. Gradient coils for generating magnetic gradient fields in all three spatial directions x, y, z, by means of which gradient coils the paramagnetic substance can be spatially encoded in a defined voxel V of the polymer precursor. A radio-frequency field generator is for irradiating RF radiation into the working zone. A control unit is configured to control the RF field generator in such a way that the spatially encoded paramagnetic substance in the voxel V can be excited by means of a field frequency of the RF radiation tuned to the paramagnetic substance in order to trigger the polymerization of the polymer precursor in the defined voxel V.

32 Claims, 2 Drawing Sheets

(51) Int. Cl.

| | |
|---|---|
| ***B29C 64/165*** | (2017.01) |
| ***B29K 105/00*** | (2006.01) |
| ***B29L 31/00*** | (2006.01) |
| ***B33Y 10/00*** | (2015.01) |
| ***B33Y 30/00*** | (2015.01) |
| ***B33Y 50/00*** | (2015.01) |
| ***B33Y 70/10*** | (2020.01) |

(52) U.S. Cl.
CPC ............... *B33Y 10/00* (2014.12); *B33Y 50/00* (2014.12); *B29K 2105/0002* (2013.01); *B29K 2995/0056* (2013.01); *B29L 2031/7532* (2013.01); *B33Y 30/00* (2014.12); *B33Y 70/10* (2020.01)

(58) Field of Classification Search
CPC ......... B33Y 10/00; B33Y 50/00; B33Y 30/00; B33Y 70/10; B33Y 80/00; B33Y 50/02; B33Y 70/00; B29K 2105/0002; B29K 2995/0056; B29L 2031/7532
See application file for complete search history.

(56) References Cited

U.S. PATENT DOCUMENTS

| | | | | |
|---|---|---|---|---|
| 5,690,109 | A | 11/1997 | Govind et al. | |
| 6,160,084 | A | 12/2000 | Langer et al. | |
| 6,183,658 | B1 | 2/2001 | Lesniak et al. | |
| 6,535,755 | B2 | 3/2003 | Ehnholm | |
| 6,808,535 | B1 | 10/2004 | Jordan | |
| 2007/0031474 | A1 | 2/2007 | Tayot | |
| 2007/0148437 | A1 | 6/2007 | Miller-Schulte | |
| 2008/0125854 | A1 | 5/2008 | Alt et al. | |
| 2008/0129295 | A1* | 6/2008 | Carlton | G01R 33/341 361/679.01 |
| 2011/0052609 | A1 | 3/2011 | Waldoefner et al. | |
| 2011/0160515 | A1 | 6/2011 | Feucht et al. | |
| 2011/0223255 | A1 | 9/2011 | Thiesen et al. | |
| 2013/0102545 | A1 | 4/2013 | Gao et al. | |
| 2015/0165225 | A1 | 6/2015 | Nadobny et al. | |
| 2017/0236639 | A1* | 8/2017 | Pieper | B22F 10/25 219/76.12 |
| 2018/0261363 | A1* | 9/2018 | Lee | B22F 10/16 |
| 2018/0273776 | A1 | 9/2018 | Ahn et al. | |
| 2019/0136176 | A1* | 5/2019 | Kawachi | C12M 35/06 |
| 2019/0263060 | A1* | 8/2019 | Goodrich | B29C 64/209 |
| 2020/0223099 | A1* | 7/2020 | Kim | H01F 1/083 |
| 2021/0299952 | A1* | 9/2021 | Xia | B29C 64/393 |
| 2021/0323070 | A1* | 10/2021 | Nlebedim | B22F 10/34 |
| 2022/0044870 | A1* | 2/2022 | Yahata | H01F 41/0253 |
| 2022/0288695 | A1* | 9/2022 | Ren | B22F 12/50 |
| 2023/0271383 | A1* | 8/2023 | Ruzycki | B29C 64/129 264/401 |

FOREIGN PATENT DOCUMENTS

| | | | | |
|---|---|---|---|---|
| DE | 199 21 088 | C2 | 8/2003 | |
| DE | 699 17 224 | T2 | 9/2004 | |
| DE | 102 02 459 | A1 | 4/2005 | |
| DE | 103 50 248 | A1 | 6/2005 | |
| DE | 10 2004 017 705 | A1 | 11/2005 | |
| DE | 10 2008 003 615 | A1 | 7/2009 | |
| DE | 10 2008 008 522 | A1 | 8/2009 | |
| DE | 10 2009 058 769 | A1 | 6/2011 | |
| EP | 0 040 512 | B1 | 1/1986 | |
| EP | 1 241 485 | A2 | 9/2002 | |
| EP | 3 292 990 | A1 | 3/2018 | |
| JP | 2666537 | B2 | 10/1997 | |
| WO | 97/38058 | A1 | 10/1997 | |
| WO | 2003/026618 | A1 | 4/2003 | |
| WO | WO-2005119286 | A1 * | 12/2005 | A61N 1/403 |
| WO | 2006/116403 | A2 | 11/2006 | |
| WO | 2009/118091 | A1 | 10/2009 | |
| WO | 2018/112472 | A1 | 6/2018 | |
| WO | 2021/055063 | A2 | 3/2021 | |

OTHER PUBLICATIONS

Plastics—the Facts 2020, "An Analysis of European Plastics Production, Demand and Waste Data", Plastics Europe—Association of Plastics Manufacturers, 2020, 64 pages.
Silvia Mannucci, et cl., Hindawi: Contrast Media & Molecular Imaging, vol. 2018, Article ID 2198703, 12 pages https://doi.org/10.1155/2018/2198703.
David Heinke, et al., Infinite Science Publishing: International Journal on Magnetic Particle Imaging, Jun. 2017, vol. 3, No. 2, Article ID 1706004, 6 Pages.

* cited by examiner

APPARATUS, SYSTEM AND METHOD FOR GENERATING A 3D STRUCTURE

CROSS-REFERENCE TO RELATED APPLICATIONS

This continuation application claims priority to PCT/EP2022/064272 filed on May 25, 2022 which has published as WO 2022/248586 A1 and also the European application number No. 21 176 035.0 filed on May 26, 2021, the entire contents of which are fully incorporated herein with these references.

DESCRIPTION

Field of the Invention

The present invention relates to an apparatus, to a system, and to a method for generating a three-dimensional (3D) structure. Furthermore, the invention relates to the use of the apparatus and also of the system.

Background of the Invention

In so-called 3D printing (additive manufacturing), the fabrication of a three-dimensional structure takes place by a layer-by-layer buildup of one or more liquid or solid materials according to prespecified dimensions and shapes. Physical or chemical curing and/or melting processes take place during the structure formation. Typical materials for 3D printing are plastics, synthetic resins, ceramics, and metals. 3D printing is characterized by a cost-effective customizability of the 3D structure with regard to geometry, material strength, and functionality—simultaneously with high capacity for automation and decentralization. On the basis of CAD-optimized image files, a controlled, reproducible, and real-time-modulatable production of three-dimensional structures by an increasingly precise material deposition in a coordinate-adapted coordinate system is thus nowadays achieved by means of a wide variety of additive method technologies.

In the field of medicine, the replacement of functional cell complexes and mechanical-supporting framework structures constitutes a major challenge. Tissue losses due to diseases, injury, chronic wear, and (radical) surgical interventions cannot always be repaired by the body's own self-healing forces. The resulting limited functionality and stability of the affected tissues, their neighboring structures, and possibly the entire body often lead to a considerable reduction in the quality of life of the person concerned and to functional limitations.

Until today, human autologous tissue replacement is considered to be the optimum in all reconstructive disciplines of medicine. It offers the characteristic advantages of the original tissue and maximum tissue compatibility due to identical immunological surface features. However, this resource is limited.

Intracorporeal stimulation methods, such as microfracturing, often lead to mechanically unstable repair tissue, e.g., fiber cartilage, and ultimately to defective healing and secondary arthrosis.

Methods for extracorporeal tissue multiplication in bioreactors are complex, expensive and must be considered as insufficient, in particular, for simultaneous breeding of various cell lines, in terms of the authenticity of their biochemical and biomechanical stimuli. This applies, in particular, to the incubation of complex 3D bioprint products, whose cell composites have recently considerably improved in detail resolution but suffer, inter alia, from a lack of early physiological adaptation.

If one considers the previously used bioprinting-technologies, shear forces and pressure gradients of the extrusion processes and long production times of the extrusion and micro-valve processes compromise cell vitality, and rheological limitations compromise the spatial resolution and cell density.

SLA and laser methods with high detail resolution and cell density in turn have cytotoxic, mutagenic and cell metabolic side effects. All common bioprinting systems are also limited in many ways for direct clinical use. This can be due to a limited penetration depth and lack of geometric adaptivity due to rigid mechanical axis or undirected wave interferences—but, in particular, also due to their still-limited number of simultaneously processed cell and material types. Ultimately, this results in insufficient stability and functionality of their products.

Artificial endoprostheses in turn constitute a compromise between mechanical durability and artificial biocompatibility. The individualized customization thereof has hitherto been carried out in standard health care only by implantation of standard sizes and standard materials—far from any real bioauthenticity. Although commercially available, popular, and stable, these implants have no adaptation or growth capacity, and often require invasive replacement operations.

All mentioned strategies for the replacement of tissue share, irrespective of their specific disadvantages, the fundamental basic conflict between the competing interests of stability and minimal invasiveness. This is because, with increasing stability of the implant, the invasiveness of its implantation, and consequently the risk of perioperative complications, increases inevitably. Thus, collateral damage of the surrounding tissue is unavoidable along the surgical access route, during the tissue harvesting, and, in particular, during the implant insertion due to the need for traumatic congruence matching of the implant and implant bed, and invasive fixation techniques. Every single collateral damage and their sum limit the local healing capacity, especially in the case of preexisting reduced regeneration capacities of the patient. This can result in an acute or chronic inadequate tissue stability and vitality, pathological biomechanics, and increased likelihood of sequel morbidities.

What is particularly dramatic as we evaluate the healing of the implant is that the corrective tissue resections, as well as the mechanical anchoring mechanisms (sutures, screws, pins, press fits) specifically damage the transition zone (interface) from the implant to the organism, with its key function for the implant integration. Structural lesions of the transition zone result directly in a limited biomimetic capacity of the implant surface. An increased release of inflammatory mediators can also occur, triggering cascaded, extremely undesirable imbalances in microcirculation, permeability, oxygen- and nutrient diffusion, cell adhesion, and cell migration. A very low implant stability, in turn, facilitates the shape-congruent lining of the tissue defect being addressed, and thus the local adhesion, but is to be considered inadequate at least for the musculoskeletal support and holding apparatus.

Considering recent research findings in the TERM field (tissue engineering & regenerative medicine), despite all experimental in vitro successes, there are fundamental hurdles for clinical application, which will be hardly overcome in the future with the conventional solution approaches.

In a time of globally increasing virulent and multi-resistant nosocomial microbes, the invasiveness and extensiveness of surgical interventions is becoming an increasingly significant risk factor and thus predictor of patient outcomes. While the compatibility of bioartificial tissue implants increases steadily, traditional allogeneic tissue products—as well as transgenic xenografts—continue to require immunosuppressive accompanying drugs which additionally weaken the defense of the recipient. At the same time, there is a widening gulf between increasing diagnostic sensitivity and specificity, accompanied by increasing understanding of premorphological early tissue damage or microinstabilities, on the one hand, and their practical treatments by means of classical operation techniques on the other hand. It is thus to be feared that minimally invasive surgery will soon run up against the limits of technical feasibility. A further minimization of collateral damage and consequential complications can only succeed in the context of novel interventional tissue replacement techniques according to the guiding medical precept of "primum non nocere."

Numerous developmental biology studies of the past years testify to the immense importance of the information content in micro-dimensional framework structures for controlling tissue regeneration and triggering of messenger cascades. As such, the 3D microarchitecture serves as a fundamental, universal morphological code of biomimetic activity, and consequently as an inductive key factor of cell adhesion, migration, differentiation and proliferation, with significant influence of structural anisotropy on the natural character of cellular performance. The spatial diversity of surface features, pore size, and materials of an implant therefore inevitably influences the localized specificity, activity, and dominance of differentiated cell populations and, depending on their extracellular matrix, consequently the mechanical properties of the regenerated structures and/or the fate of the implants integrated to different degrees—and ideally adopted. Bioartificial 3D skeletons thus serve the cells in vivo as a micro-ecological niche, i.e., as an incubator chamber, a placeholder, and a framework structure, and also as the foster-mother for the remodeling—that is, as an instructive differentiation aid. Overall, therefore, they serve as a guarantee of an adequate physiological healing process, characterized by an authentic and specific tissue buildup and the timely sequential exchange of temporary for authentic tissue complexes, with the aim of a healthy load capacity and physiological functionality.

SUMMARY OF THE INVENTION

Object of the Invention:

It is the object of the invention to specify an apparatus and a system by means of which a 3D structure can be generated (manufactured) in a simple and highly precise manner in vitro and in vivo, i.e., in the human/animal body, with a high detail resolution. In addition, it is the object of the invention to specify a method for generating a 3D structure, as well as uses of the apparatus and the system.

Solution of the Object According to the Invention:

The object relating to the apparatus is achieved by an apparatus having the features specified in claim 1, and the object relating to the system is achieved by a system having the features specified in claim 11. The use of the apparatus and/or of the system is specified in claim 22. The method (MRiP) according to the invention is specified in claim 24.

Preliminary Remarks:

In the following description of the invention, the terms prepolymer and polymer precursor are used synonymously.

Apparatus:

The apparatus according to the invention serves to generate a three-dimensional (3D) structure, and comprises: a magnetic field generator for generating a static magnetic field $B_0$ in a working zone of the apparatus in which a polymer precursor with at least one paramagnetic substance can be arranged; gradient coils for generating magnetic gradient fields in all three spatial directions x, y, z, by means of which gradient coils the paramagnetic substance can be spatially encoded in a defined voxel V of the polymer precursor; a radio-frequency (RF) field generator for, preferably pulsed, irradiation of RF radiation into the working zone; and a control unit which is configured to control the RF field generator in such a way that the spatially encoded paramagnetic substance in the voxel V can be excited by means of a field frequency of the RF radiation tuned to the paramagnetic substance in order to trigger the thermal polymerization of the polymer precursor, preferably solely in the voxel V.

The apparatus according to the invention allows an additive inductive multidimensional generation of any 3D structures. This is produced by precise RF stimulation of the paramagnetic substance in electromagnetic resonance niches which are generated in a location-specific manner, in particular, on the basis of high-resolution image data, by targeted superposition of magnetic gradient fields within a more or less liquid thermosensitive polymer precursor. The apparatus thereby allows the production of 3D structures of any geometry, structure, surface texture, and—depending on the materials used—also each with predefined material properties. One-time and repeated post-processing procedures of the 3D-generated product are possible.

According to the invention, the apparatus can in particular, comprise a device for image data acquisition or image acquisition. In other words, an apparatus for obtaining image data. Particularly preferably, the apparatus comprises an MRT device. MRT devices can be functionally expanded by suitable programming of their control software to form an apparatus according to the invention. It goes without saying that this is basically also possible in already existing MRT devices. Furthermore, the MRT device allows the acquisition of image data from the working zone, thus of the polymer precursor, of the (possibly only partially generated) 3D structure, and, if necessary, also of the corresponding surroundings (in particular, tissue structures in vivo).

According to the invention, the apparatus can additionally or alternatively comprise a computer tomograph (CT), a digital volume tomograph (DVT), a sonographic device, a laser scanner, and/or a positron emission tomograph (PET) in order to acquire suitable image data from the aforementioned regions. According to the invention, the device for obtaining image data can also comprise one or more cameras, in particular CCD (charge coupled device) cameras or infrared cameras (thermographic cameras).

The control unit of the apparatus preferably has an operating mode for obtaining and evaluating image data, in particular magnetic resonance tomography data, from the working zone. As a result, image data from the polymer precursor, the (optionally only partially completed) 3D structure, and, if necessary, also the corresponding surroundings (in particular, tissue structures in vivo) can be obtained. The apparatus thereby allows imaging diagnostics to be combined with the additive method for generating the 3D structure, and/or to combine the logic of electromagnetic and biomimetic induction principles.

If the apparatus comprises an MRT scanner, MRI-based thermometry data can be obtained from the working zone, i.e., from the polymer precursor, the (optionally only partially completed) 3D structure, and, if necessary, also the corresponding surroundings (in particular, tissue structures in vivo). These thermometry data can be taken into account when generating the 3D structure, for example when determining the duration or intensity of the RF field to be irradiated to excite a defined voxel.

If the apparatus or the MRT device is configured for so-called magnetic particle imaging (MPI), the distribution and concentration of the paramagnetic substance within, for example, a spatial volume, of the prepolymer or of the 3D structure can be detected metrologically. A sufficiently homogeneous distribution and sufficient concentration of the paramagnetic nanoparticles in the prepolymer/in the 3D structure can thereby be determined. This is advantageous for quality assurance in manufacturing the 3D structure. On the other hand, the spatial distribution and quantity of the prepolymer/the 3D structure in the working zone can thereby be determined in a simplified manner.

In additive manufacturing methods, thermodynamic phenomena are known to represent an important artifact source, the effects of which must be limited to the greatest possible extent. This is to prevent both micro-dimensional losses of the detail resolution and macro-dimensional structure inhomogeneities and irregularities of the 3D structure.

Thermosensitive sequences in the context of so-called MRI-assisted HIFUS treatments (highly focused ultrasound) have recently proven their clinical practicability and reliability. In particular, the proton resonance method is characterized by a high spatial, temporal and thermomagnetic resolution and reliability, and is therefore also suitable for monitoring the manufacturing process in order to quickly detect disadvantageous heat dissipation and/or accumulation in three-dimensional space. According to the invention, the apparatus can be designed to carry out such thermosensitive sequences.

The apparatus preferably has a software application by means of which absolute temperature values can be derived from the data obtained during the thermosensitive sequences and can preferably be coded in color, user-defined topographical and thermal threshold values can be coupled to alarms in a location-specific manner, and the compliance with precise exposure dose limits can be automated or regulated semi-autonomously.

While a reduction in the detail resolution during the generation of the 3D structure is attributable to blurring of the polymerization limits, which occur due to thermodynamic, voxel-exceeding heat conduction during the generative process, macro-dimensional aberrations occur on the basis of coarse heat accumulations primarily only after the end of the polymerization, resulting in shrinkage and distortion due to the material relaxation during the cooling. Experience has shown that these phenomena are less pronounced in inductive heating than in other thermal curing processes and can be further reduced by preheating the prepolymer and postheating the polymer. In the case of in vivo production, the physiological body temperature and the relatively low transition thresholds of the prepolymers in comparison with the industrial (ex vivo) manufacturing of 3D structures mean that only very minimal temperature gradients are expected, which, for example, could be overcome via accessory heat sources (e.g., infrared diodes, UV/laser diodes, high-energy radiators, hot air) and/or a fractional heating, optimized by segmentation methods and thermometry thresholds.

An annealing—i.e., preheating—of the prepolymer, and optionally also of the entire site, and/or in vivo of the anatomical region, serves in this case to reduce the temperature gradients and homogenize the temperature profile, and also specifically to reduce energy quantities to be applied inductively, and thus to reduce the risk of aberrant heat dynamics on the micro- and macro-level. This can be understood as a preconditioning of the prepolymer. The more clearly and narrowly the transition threshold is defined, the more precise the generative accuracy. In addition, the lower the thermal conductivity of the prepolymer+polymer used, the lower the risk of heterotopic heat accumulation and thus of a dystopic polymerization, and the higher the thermal resolution, and consequently the structural resolution.

In order to avoid macrodimensional and also microdimensional heat accumulations, the generation of large solidity and volume differences, concentrated material masses, strong offsets, and high temperature differences in the polymer product should be avoided. On the other hand, the spatial resolution increases in the prepolymer with the steepness of the temperature gradient between inductively heated, isolated individual voxels relative to their surroundings, which is why functional reliefs and edge borders, and even cooling measures, should be considered for detailed optimization at relevant boundary zones. A certain stimulation redundancy of the oscillators and/or inertia of the polymerization can also reduce the thermal artifact susceptibility to enhance the structural resolution. In the multi-shot concept, a plurality of stimulative RF pulses is correspondingly necessary in order to reach the transition temperature—tightly tuned to the thermal conductivity of the prepolymer—resulting in a steeper temperature gradient to the corresponding adjacent voxel and thus a higher selectivity.

With increasing curing of the polymer, the structural conditions change with considerable influence on the heat dissipation. The material continuity and solidification which varies by zone results, with progressive curing of the polymer, in an increasingly heterogeneous thermal system in which, due to cumulative effects, overheated and overcooled zones are produced. These zones must be preemptively anticipated in calculations and proactively compensated for in order to avoid dystopic polymerizations to the greatest possible extent. This is achieved by assessing all described phenomena and taking into account all mentioned influencing factors—on the one hand by selecting a suitable thermoresponsive prepolymer (-composite) with a favorable thermal transition threshold and advantageous thermal conductivity (see above), as well as in particular by targeted modulation of the RF pulse duration and intervals, and the temporal and spatial perception thereof in three-dimensional space by dynamic adaptation of the resonance-vulnerable voxel size and voxel position by means of dynamic magnetic field gradients.

A longer continuous local excitation results in a steeper temperature gradient than a repetitive short, pulsed excitation, and the sequential excitation of two immediately adjacent voxels leads in sum to a locally higher heat accumulation than the stimulation of two voxels remote from one another.

The polymerization of the polymer precursor can potentially limit the oscillation capacity and the resonance specificity of the (nano-) oscillators with a self-terminating effect. Generally, the thicker and larger the 3D structure to be produced, and the stronger their material, the higher the risk of heat accumulation; the smaller, slimmer, and more discontinuous the 3D structure to be produced, the faster a temperature equalization takes place. For this reason, it is all the more important to take into account the effects that can be calculated therefrom at the earliest possible time, to incorporate them into the CAD design of the 3D structure to be produced and into the optimization of the sequence algorithm, and, if necessary, to adaptively regulate them in real time.

This also includes taking into account special shapes and structural interruptions as thermal conductors or thermal obstacles in the CAD construction plan, in order to channel or to obstruct heat-conducting phenomena, specifically to generate locally stresses and to dissipate them elsewhere.

Irrespective of this, a higher concentration of the paramagnetic substance or of the (nano-) oscillators concentration of the prepolymer theoretically leads to a higher inductive spatial resolution.

An increase in the procedural ambient pressure, accompanied by a reduced prepolymer fluctuation at the same time, can also promote inductive spatial resolution. Although macroaberrations arise across layers, especially during cooling, it also occurs even within the layers as early on as the material consolidation. This phenomenon can also be effectively counteracted by increasing the ambient pressure and providing sufficient polymer precursor reserves. By means of the apparatus according to the invention, a "real 3D" manufacturing method can thus be realized, and the prepolymer precursor can be polymerized in all spatial directions. The traditional layering phenomena are neutralized in this case.

The control device is preferably configured, in particular, programmed, to control all operating parameters of the apparatus relevant to generating the 3D structure, on the basis of predefined CAD data of the 3D structure.

Particularly preferably, the control unit is configured, in particular programmed, by means of a repetitive imaging utilizing: magnetic resonance tomography; computer tomography; digital volume tomography, sonography; laser scanning; and/or positron emission tomography; and/or by means of a CCD camera and/or an infrared camera, to compare the image data of the polymer precursor and/or the partially completed 3D structure with the CAD/CAM data and, if the findings exceed a defined deviation of the image data from the CAD/CAM data, to adapt the operating parameters and/or CAD/CAM data for producing the remaining 3D structure in such a way that (further) deviations from the CAD/CAM data during the production of the rest of the 3D structure are counteracted. In other words, the control unit is configured to align the desired/actual state of the polymerization of the polymer precursor by means of repetitive image acquisitions, and to continue controlling the further production process of the 3D structure on the basis of the data obtained in this way. Optimally, MRI can be used for this purpose, although the above-mentioned alternative imaging devices—optionally also multimodal, combined device—can be used.

According to the invention, the apparatus can also have a device for controlled cooling of the 3D structure, by means of which cold air and/or a suitable cooling fluid, for example water, can be supplied to the 3D structure. The formation of undesired damage, in particular strain cracks, can thereby be counteracted in the 3D structure.

The apparatus according to the invention thus enables overall an additive manufacturing method of 3D structures, which, based on the technique of resonance niche induction, can be referred to as magnetic resonance induction polymerization ("MriP").

The 3D structure that can be generated by means of the apparatus can be any product made of a polymer or polymer composite material. The 3D structure can thus be a machine element, for example. In particular, axles, shafts, bearing elements, gear parts, seal elements, connecting elements, housing (parts), etc. can be contemplated. The 3D structure can, in particular, also be an adhesive, soldered, or welded connection of two or more components or a coating of a component. The 3D structure may be made of an elastomer, a thermoplastic, or a thermosetting polymer, or may comprise one of these materials.

The 3D structure can also be a medical product, for example an epithesis, an orthosis, a bandage, a tooth brace, a tooth veneer, a ventilation tube, a tissue adhesive, a medical implant, or a (bio-) artificial structure for a tissue or organ replacement. Furthermore, the 3D structure can be an everyday object, for example jewelry, a timepiece housing, a toy, a carry container, dishes, cutlery, an electrically insulating or electrically conductive layer, or very generally a coating of any other structure.

On the basis of precisely controlled induction phenomena, modern material sciences, and imaging modalities, Cax, nanotechnology, stem cell research, and development biology, the apparatus according to the invention can transfer, by means of the magnetic resonance induction polymerization possible as a result, the potential of generative 3D processes into the medical context of tissue engineering, and transfer it directly into the living body, making use of magnetic resonance for diagnosis, navigation, surveillance, and generative force.

In situ (bio-) production offers from the very beginning all advantages of natural tissue regeneration within a physiological, bioresponsive environment, and thus solves the primary problems of conventional tissue replacement products and conventional bioreactors—such as lack of stability, lack of integrativity, lack of adaptivity, lack of interactivity, and inadequate vitality. It follows from this that precise stimulation of the paramagnetic substance via the design of the inner structure and surface texture of the polymer 3D structure exerts direct and indirect influence on the quality and intensity of its interactions with the receiver organism. Thus, mastery of electromagnetic induction results in mastery of biomimetic induction, and consequently the bioactive competence of the implant and the bioauthentic capacity of the regenerated tissue structures.

The apparatus according to the invention carries the key for universality and the enormous potential to produce a 3D structure which is highly flexible both on microtopographic and macroarchitectural levels, suiting the individual diversity of tissue defects and tissue recipients requiring treatment. By means of the apparatus, a 3D structure can be produced which authentically emulates the natural anisotropy of hierarchically organized biological tissue and the deterministic complexity of bioartificial interfaces, in order to create the biomimetic features at the earliest possible moment, and durably, that are required for long-term functionality of the implant in the overall systemic environment.

The apparatus can be used, for example, for the in vivo production of the 3D structure. In this case, a seamless linking of the 3D structure to be produced with body's own structures or structures foreign to the body can be realized, i.e., the anchoring thereof at the target location with the surrounding tissues. The apparatus thus allows direct in situ 3D bioprinting in the living organism. The optional vitalization of the 3D structure by passive and/or active cell colonization can, for example, be realized in a contactless and minimally invasive manner.

If the apparatus has at least one, or a plurality, of the above-mentioned devices for the image (data) acquisition, an image-controlled or image-navigated application of the polymer precursor at the predetermined destination is thereby made possible. This is advantageous in particular, in the case of in vivo production of the 3D structure.

It should be noted that the apparatus according to the invention, when used in the medical field, allows an 8D production of the 3D structure in a further sense. That is, it is a technology which can add material in all spatial directions ("real" 3D), without constraint to axes. For in vivo production, the 3D structure can interact with its surroundings (4D), provide instructions (5D), be vitalized by cells (6D), and can accordingly be capable of transformation up to the moment of complete biological integration (7D). And it can also be modified without contact and optionally multiple times from the outside (8D). It should be emphasized in particular, here that "real" 3D processing ensures a homogeneous isotropic, i.e., uniform-load-bearing capacity of the 3D structure, whereas classic 3D print products generally have a direction-dependent mechanical load-carrying capacity depending on the traditional construction axis (z-axis).

In the medical context, the apparatus according to the invention and/or the MRiP 3D method according to the invention serves the purpose of repairing, reconstructing, respecting, correcting, and optimizing the integrity and interactivity of functional anatomic tissue structures, in order to stimulate and amplify authentic regenerative processes. This applies, in particular, to very small anatomical functional units and very large tissue volumes, which hitherto have been deprived of a sufficient "restitution ad integrum" with conventional techniques.

By means of the apparatus according to the invention and/or the system according to the invention, in vivo production of the 3D structure is possible even for the groups of patients with a risk profile which has hitherto limited or not allowed invasive therapy methods.

The principle of contactless heat generation by inductive power transmission by means of alternating electromagnetic fields and/or RF radiation is generally known, and has been used for decades in physical medicine, as a field other than industrial manufacturing processes. The fact that the coupling of magnetic nanoparticles to electromagnetic alternating fields in the human body can produce biologically relevant and reliably therapeutic thermal phenomena is proven not least of all by the FDA approval of oncological interstitial hyperthermia.

However, an instrumentalization of these methods for additive structural manufacturing using inductive polymerization of thermosensitive polymer composite preparations to form multidimensional structures has never been described. This may be due to the fact that high-precision focusing of electromagnetic fields has only been possible up to now, even under laboratory conditions, with disproportionately great technical effort. A rough focusing, as can be achieved, for example, by means of frequency-coherent amplifiers, is not sufficient for precise additive technologies, in contrast.

Since electromagnetic induction, however, in contrast to the established traditional methods of contactless energy transmission (UV, IR, ultrasound, laser), does not come with undesired interference and absorption phenomena at increasing travels distance (penetration depth) or tissue transition, and does not have any biologically damaging potential, while maintaining legal dose limit values and frequency spectra, and does not require a protective atmosphere or rigid, mechanical guide systems, it should be regarded as the ideal energy source for contactless 3D production, in particular also for in situ biofabrication. The extraordinary universality of MRiP results from its unique multiparametric strategy for building structures up of the smallest possible subunits, resulting in maximum freedom of design and adaptability.

The apparatus according to the invention, the system, and also the method (MRiP) for generating the 3D structure now provide for the first time a practical approach to how inductive energy depositions can also be implemented, modulated, and used in a targeted manner for controlled additive structure construction by means of undirected electromagnetic alternating fields (RF field).

In the natural state, all sufficiently small paramagnetic substances, in particular superparamagnetic nanoparticles, for example nanoparticulate magnetite particles, as nano-oscillators, have their own, individually unique, minimum oscillation moment defined by their electromagnetic milieu and their individual energy content. In a homogeneous static magnetic field whose field strength is a multiple of the electromagnetic environment of the oscillators, all oscillators align their rotational moments parallel or antiparallel to the magnetic field lines of the static field and can be excited to thermogenic oscillations by an external RF field with a frequency that corresponds to the resonant frequency $f_0$ of the paramagnetic oscillators, or substantially corresponds thereto.

The steepness and speed of the dynamic gradient fields of the apparatus can be specified in at least 3 spatial directions in order to define the corresponding voxel dimension (spatial/time) and the voxel distribution (spatial/time).

According to the invention, the working zone of the apparatus can be arranged within a housing or enclosure of the apparatus. In this way, a defined working environment can be provided and maintained for generating the 3D structure. For example, the temperature, the composition of the atmosphere (working atmosphere), the atmospheric pressure in the working zone, and also the moisture of the working atmosphere directly surrounding the working zone can be simplified and adjusted in a cost-effective manner. The housing can consist of plastic, for example in the form of a plastic film, of glass, or of a different MRI-suitable material.

Particularly preferably, the apparatus has a pump by means of which the working zone can be filled with a working atmosphere specified for the corresponding manufacturing process—and/or a subatmospheric pressure and/or a vacuum can be built up in the working zone.

According to the invention, the apparatus can have a temperature control device for controlling the temperature of the working zone and/or the polymer precursor arranged in the working zone. By means of the temperature control device, the polymer precursor can be cooled as needed in order, for example, to counteract an undesired uncontrolled polymerization of the polymer precursor outside of the voxels selected/determined for polymerization, in advance and/or during the production of the 3D structure. By means of the temperature control device, the working zone and/or the polymer precursor arranged therein can, however, also be heated, i.e., "initiated", as required in order to promote polymerization thereof.

Polymer Precursor:

The invention also relates to a polymer precursor having at least one paramagnetic substance for the production (generation) of a 3D structure.

According to the invention, the polymer precursor comprises monomers and/or oligomers and/or polymers which polymerize by way of a thermal polymerization, i.e., by the action of thermal energy.

The polymer precursor can, in particular, comprise so-called biopolymers. These are characterized by high biocompatibility, high bioactivity, and cell binding capacity. According to the invention, for example, polysaccharides, glycosaminoglycans, polypeptides and/or proteins are suitable here. Especially alginates, hyaluron, collagens/gelatins, chitosan, fibrin, silk fibroin, cellulose, and even derivatives of the human extracellular matrix (ECM derivatives) and so-called bio-artificial polymers are conceivable. Marine collagens, for example from fish waste (fish gelatin metacrolyl=FGelMa), are also conceivable.

Artificial polymers in turn have a high mechanical stability and precisely modulatable properties (e.g., defined degradation rate). Conventional materials of biotechnology+pharmacology, as well as increasingly established substances of the plastics processing industry, can be contemplated as well, of which some suitable materials are mentioned in the following: PLA (polylactic acid), PEG (polyethylene glycol), PCL (polycaprolactone, a very good starting material for inorganic bioceramics), PGA (polyglycolic acid), PLGA (poly(lactide-co-glycolide), PEO (polyethylene glycol), PPO (polyphenylene oxide), PU (polyurethane), PEEK (polyether ether ketone), polyamides (nylon; +/−polyester), PCU-Sil (polycarbonate-based urethane silicones), PUU (polyurea-urethanes), SMP (shape memory polymers), acrylonitriles (e.g., ABS: acrylonitrile-butadiene styrene), block copolymers, liquid-crystal polymers.

In order to use the advantages of both groups, the polymer precursor according to the invention can comprise a multi-material mix (e.g., PEG collagen hydrogels).

The paramagnetic substance preferably comprises paramagnetic particles, in particular, in the form of paramagnetic microparticles or nanoparticles. The paramagnetic substance is preferably excitable to oscillatory movements in a highly specific frequency-selective manner, i.e., by irradiation by an RF field with a defined frequency or a defined frequency band. As a result of these oscillatory movements of the paramagnetic substance, a thermal energy input into the polymer precursor can be achieved for polymerization of the polymer precursor.

The concentration of the aforementioned particles is preferably >1000 particles per milliliter of the polymer precursor, in particular >10,000 particles per milliliter of the polymer precursor. A reliable and homogeneous polymerization of the polymer precursor in each spatially encoded voxel of the polymer precursor is thereby ensured during the production process. Depending on the 3D structure to be produced from the polymer precursor and/or the composition of the polymer precursor, the concentration of the particles can be adjusted accordingly. According to the invention, the concentration of the particles can be up to $10^{17}$ particles per milliliter of the polymer precursor. As a result, the smallest 3D structures can also be additively manufactured now, and with a hitherto impossible detail resolution.

According to the invention, the paramagnetic substance preferably comprises metal particles. The particles can, for example, be made of magnetite ($Fe_3O_4$) or a silver halide ($Ag_nX_n$).

Nanoparticulate magnetite particles or greigite particles ($Fe_3S_4$) are found, for example, in so-called magnetosomes, for example of bacteria or fungi. These magnetosomes formed by biomineralization are characterized by a particularly small scattering of the average particle size of their nanoparticulate particles. Within the scope of the invention, such magnetosomes can be used, preferably purified or optionally with the prokaryotic/eukaryotic cells in which the magnetosomes are contained, as a paramagnetic substance. Nevertheless, the known magnetosome nanoparticles are composed of a material that is ferromagnetic per se they show with paramagnetic or superparamagnetic properties at a size of less than about 50 nm. For more on this topic, see, e.g., Manucci S et al (2018). magnetosomes extracted from magnetospirillum gryphiswaldensae as theranostic agents in experimental model of glioblastoma. Contrast Media Mol Imaging Jul. 11, 2018:2198703. doi: 10.1155/2018/2198703 Heinke D et al (2017). MPS and MRI efficacy of magnetosomes from wild-type and mutant bacterial strains. Int J Mag Part Imag Vol 3 No 2 (2017), P. 1-6) Article ID 1706004

According to one embodiment of the invention, the paramagnetic substance is preferably suspended in the polymer precursor. A distribution/suspension of the paramagnetic particles in the polymer precursor as homogeneously as possible is advantageous.

According to an alternative development of the invention, the paramagnetic substance can also be bound at least partially or completely to monomers/polymers of the polymer precursor. Such metal organyls or organometallic compounds generally have a polar covalent bond between a carbon atom and at least one metal or electropositive element atom.

According to a particularly preferred development of the invention, the paramagnetic particles of the polymer precursor can differ from one another at least partially in their material properties or in their specific chemical composition and/or size.

With regard to the biocompatibility of the particles, the particles can each have a coating. The coating of the particles can comprise titanium, for example. Other biocompatible coating materials, such as polyether ether ketone (PEEK), polyetherimide (PEI), polycarbonates, acrylonitrile butadiene styrene, polylactides (PLA), polyhydroxyacetic acid, polyglycolic acid are also conceivable.

Furthermore, the polymer precursor can comprise (in addition to the paramagnetic) according to the invention one or more additives (additives). The additives can be organic and/or inorganic additives.

The capacity of optional biological, chemical, physical, and pharmaceutical additives should not be underestimated. These serve, for example, as inductors, promoters, catalysts, and terminators of the (bio-) chemical reactivity, the homogenization and stabilization of the medium or the resonance conditions, and thus also to artifact reduction. Equally, they can lead to an increase as well as to the reduction of the electrical or thermal conductivity or insulation within the polymer precursor, and thereby influence the polymerization positively or negatively, provide sensitive internal and external zones, and optionally simplify post-processing.

In particular, nanoparticles in the smallest amounts can dramatically change the original properties of materials and their end products, to functionalize them and (bio)activate them (e.g., Au, Ag, montomorillonites, laponites, hectorites, silica, $Fe_2O_3$, $Fe_3O_4$, graphene, graphene oxides, nanocellulose, LDHs (layered double hydroxides, pyrroles, . . . ).

According to a development, the additives can function as adsorbants, whether to bind or convert toxic or counterproductive metabolites and catabolites, undesired messengers or pain mediators, in order to prevent, for example, immunological defense and sensitization cascades or infections.

Suitable additives can allow the rheological properties—among other things the surface tension—of the polymer precursor to be influenced in order to maximize their injectability and microadhesiveness.

Other suitable additives in turn can help to modulate or limit the final consistency of the 3D structure specifically (e.g., fillers). Likewise mentioned are additives in the form of biologics for cell activation and control, such as growth factors and immunomodulators (e. g., interferons), radio modulators for enhancing radiotherapies, and cytostatic agents, as well as visualization aids such as contrast agents or other externally detectable and quantifiable markers.

The additives can thus in particular be selected from the group of: fibers; dyes; antibacterial substances; growth factors; nanoparticles/tubes; mineral fillers (e.g., tricalcium phosphate cement, nano-hydroxyapatite, bioactive glass); metallic materials (e. g., silver, Gold, magnetite ($Fe_2O_3$, $Fe_3O_4$)—e.g., SPION: superparamagnetic iron oxide nanoparticles, Gd-chelates/conjugates); glycosaminoglycans; so-called MMC substances (for so-called macromolecular crowding; e.g., dextrans or fico) (sucrose-epichlorohydrin copolymer)); polypeptide motifs such as—RGD sequences (arginine, glycine and aspartic acid), which are present, for example, in proteins of the extracellular matrix (e.g., in fibronectin and vitronectin); IKVAV+-YIGSR (Laminin); and promoters (terminators, inhibitors, catalysts, sensitizers, immunomodulators (such as VGF or the molecule JNK3).

The aforementioned additives can be present as free substances, bound to substances, or temporarily fixed to transport molecules or in thermosomes.

The polymer precursor can in particular have a liquid form or gel form. Particularly preferably, the polymer precursor has a viscosity which is between $10^2$ and $10^6$ mPa·s.

According to the invention, the polymer precursor can also be present in the form of a so-called "Squid". Such squids are preformed, incompletely cured polymer precursors.

According to a preferred development of the invention, the polymer precursor is non-toxic to humans. The polymer precursor can thereby be used in the human body for in vivo 3D production.

The polymer precursor is very particularly preferably degradable in the non-polymerized state in the human and/or animal body, for example by endogenous enzymes.

System:

The system according to the invention comprises an apparatus described above for producing a 3D structure, and the polymer precursor explained above with at least one paramagnetic substance, in particular superparamagnetic metal or magnetite particles.

MRiP Method:

The method according to the invention for generating the 3D structure has the following steps:

a. defining (102) CAD/CAM data (40) for the 3D structure to be produced (30);
b. providing (104) a polymer precursor (28) comprising a preferably homogeneously distributed paramagnetic substance;
c. introducing (106) the polymer precursor (28) into the working zone of the apparatus (12);
d. spatially encoding (108) a voxel V within the polymer precursor (28) as a function of the CAD/CAM data (40) by applying magnetic gradient fields;
e. polymerizing (110) the polymer precursor (28) in the at least one spatially encoded voxel V by irradiating (112) RF radiation (42) by means of which the paramagnetic substance (32) is excited to oscillations in the corresponding voxel V; and
f. subsequently sequentially spatially encoding (108) further voxels V, preferably spatially adjacent to one another, in the polymer precursor (28) as a function of the CAD/CAM data (40), and polymerizing (110) the corresponding further spatially encoded voxels V by irradiation (112) of RF radiation (42) by means of which the paramagnetic substance (32) is excited to oscillations in the corresponding further voxel V.

In the additive manufacturing method according to the invention for the 3D structure, the spatial resolution is based on the inductive magnetic resonance phenomena of an interplay of electromagnetic resonance isolation and resonance stimulation. Diagnostic or analytical MR methods use this strategy. However, no specific resonance-frequency-selective, thermogenic, paramagnetic nanoparticles have hitherto been used which are put into a thermogenic oscillation by RF excitation and thus induce a polymerization of the polymer precursor, i.e., induction of chemical bonds in the thermosensitive polymer precursor, which is limited locally to the spatially encoded voxel of the polymer precursor.

The additive manufacturing method proposed here allows a continuous volume-gradation of the polymerization (less than, equal to, and greater than a conventional layer dimension) of the polymer precursor, i.e., a high-precision, punctiform, and also "en bloc" polymerization and thus curing of the 3D structure to be produced.

An efficient 3D manufacturing of any, in particular, bioartificial, structures and their modification is made possible in this way. The precise RF stimulation of frequency-selective thermal nanooscillators in electromagnetic resonance niches, which are generated in a location-specific manner, preferably also on the basis of high-resolution image data, by targeted superposition of magnetic gradient fields within a more or less liquid thermosensitive polymer precursor, enables, as already explained, the production of 3D structures of any geometry, configuration, and complexity, and, depending on the materials used, also of any consistency—individually, in vitro and in vivo. The strategy of building structures from the smallest possible subunits results in maximum freedom of design and adaptability of the method.

This is possible with detail accuracy and speed that was not possible until now. The method can enable new routes for the production of machine elements, medical products, in particular in medical and biotechnological biofabrication, and even in the case of in situ bioprinting. Especially because the method (MRiP) according to the invention enables a precise surface design and a seamless linkage or anchoring with other structures. As a result, a simplified and more reliable vitalization by passive/active cell colonization can be promoted when the 3D structure is implanted. In the medical context, MRiP can enable implants to be produced which repair, reconstruct, respect, correct, and optimize the integrity and interactivity of functional anatomical overall structures, in order to stimulate and amplify natural regenerative processes.

A rough focusing, as can be achieved, for example, by means of frequency-coherent amplifiers, is not sufficient for precise additive technologies. In contrast to the established traditional methods of contactless energy transfer by means of UV/IR radiation, ultrasound or laser, electromagnetic induction displays—neither for increasing travel paths in the polymer precursor and/or in the tissue (penetration depth)

nor at material transitions—relevant undesired interference and absorption phenomena. In addition, electromagnetic induction does not have a biologically damaging potential within legal dose limits and frequency spectra; and no protective atmosphere or rigid, mechanical guide systems are required per se. It is therefore to be regarded as an ideal energy source for contactless in vitro and also in vivo biofabrication.

The MRiP method according to the invention now offers for the first time a practical approach to how inductive energy depositions by means of undirected electromagnetic alternating fields (RF field) can be locally realized, modulated, and used in a targeted manner for controlled additive structure manufacturing.

In the natural state, all superparamagnetic oscillators have, in a (standardized) thermosensitive polymer precursor, e.g., a polymer composite gel, a unique minimum oscillation moment defined by their electromagnetic environment and their individual energy content.

In a homogeneous static magnetic field, whose field strength is a multiple of the electromagnetic environment of the paramagnetic oscillators, all oscillators align their rotational moments parallel or antiparallel to the magnetic field lines of the static $B_0$ field, accompanied by a synchronization of their resonance frequency sensitivity for alternating field pulses, which, in addition to material, polarity, and configuration of the oscillators, depends proportionally on the field strength of the homogeneous magnetic field. This means that, for each field strength, only a single specific frequency exists, which stimulates all correspondingly configurated oscillators at a maximum—the so-called resonant frequency. Under resonance conditions, all susceptible oscillators thus have a maximum energy absorption capacity with regard to the specific radio-frequency alternating field, resulting in a significantly increased oscillation movement which is converted into thermal energy due to resistance and friction effects with minimum coupling distance. As in nuclear magnetic resonance tomography for slice selection and location coding, dynamic gradient fields in at least 3 spatial directions serve MRiP for "indirect focusing" of these radio-frequency pulses. These magnetic fields are characterized by a continuous increase or decrease in the corresponding magnetic field strength along their characteristic axes [x, y, z] relative to the static permanent magnetic field and the polymer precursor exposed in the working zone of the magnetic fields.

A gradient field introduced by special coils in the x-axis thus superimposes the previously homogeneous, permanent static $B_0$ field, and thus leads to a linear increase or decrease of the total static field strength along the x-axis. If technically feasible, steeper nonlinear gradients would be advantageous in order to amplify the differentiation of neighbor voxels. The same applies for each introduced gradient field along the y-axis and z-axis, with the result that each defined voxel of the total volume of the working zone, and thus of the polymer precursor, or theoretically each oscillator in three-dimensional space, has its individual electromagnetic niche in the point of intersection of the at least 3 gradient fields.

Thus, if the magnetic micro-environment of each oscillator or voxel differs linearly from the magnetic micro-environment of its neighboring oscillator or voxel in all spatial directions, then each individual oscillator or each voxel possesses its own, completely unique resonant frequency, and can consequently be individually addressed and selectively excited as a result. In this case, the steepness of the gradient fields defines the edge lengths of the voxels in all 3 spatial directions, optimally by simultaneous total superposition of their local field strengths—alternatively sequentially, e.g., using the inverse Fourier transform. In contrast to all conventional additive methods, this allows both, either polymerization of individual voxels or of contiguous volume units, as a multi-voxel-processing, i.e., "en bloc" polymerization.

Instead of a single external heat source, each nanooscillator thus represents an autonomous heat source (with minimum coupling distance), the effect of which would result without addressing gradient fields in a three-dimensional thermal grid-type heating pattern made of initially multiple isomorphic and isothermal heat islets with temperature maxima in each case directly around each individual oscillator. In an otherwise closed, perfect system, the characteristic power absorption of the oscillators, their efficiency, and the material-specific heat conduction of the polymer precursor define the dimension, dynamics and duration of heat propagation up to the point in time at which a globally homogeneous heating of the total volume is achieved, depending on pulse intensity and pulse periodicity—which can be controlled by the user continuously in real time.

In practice, heat-conducting phenomena lead to a centrifugal temperature drop around each stimulated oscillator, corresponding to a thermodynamic penumbra dependent on the ambient conditions. With increasing excitation over time these thermal islets tend to conflux, to equalize, or to mutually amplify each other.

Proactively utilizing the described principles and influencing factors listed below, these effects can be locally amplified or reduced by the user by focused stimulation of individual oscillators (groups) in order to modulate the final heat patterns, and consecutively the detail resolution and quality characteristics of the product (e.g., functionality, durability), at points or zonally.

Differences in the resonance sensitivity thus allow a targeted spatially selective excitation of thermal nanooscillators (paramagnetic substance) (in vitro and/or in vivo) and consequently a high-precision generative manufacturing of complex 3D structures on the basis of differentiated energy absorption patterns and location-specific reproducible temperature profiles by controlled variation of the spatial and temporal resonance conditions. The thermal effects of electromagnetically inductively stimulated nanooscillators enable, in addition to the modulation of the internal polymer cohesion, in particular also regulating the adhesion of the 3D products by microscopic structural interlocking (microadhesion) to foreign surfaces—assuming a primary, expedient rheology of the polymer precursor.

For implants, these effects can be supplemented in the transition zone to the organism (interface) optionally by discontinuous thermocoagulating adhesive effects, resulting in a continuous, seamless regenerative healing. In vivo, this can be accompanied by post-inflammatory repair or post-necrosis focal, interconnecting scarring. In addition, site-specific inductive effects can beneficially precondition the implant bed, i.e., the base of the wound, in advance, e.g., by thermal microdebridement, hemostasis, and denervation.

The special charm of the method according to the invention is in the subtle, multi-parametric controllability of the stepwise organization phases of the product structure in real time, resulting in maximum process control, customizability and quality of outcomes.

The basic prerequisite for this is a differentiated predictive calculation of the energy doses to be applied in all spatial directions for temperature-dependent material solidification. The modulation of the energy dose transmitted per volume unit is achieved primarily by the target-oriented adaptation of the electromagnetic induction parameters and the temporo-spatial algorithmic variation of the resonance conditions, which results from the interaction of the static magnetic fields with the dynamic magnetic fields.

In this case, undirected RF stimulation pulses, by way of example with a wavelength in the multi-digit centimeter range (MRT diagnostics), can easily selectively excite voxels in the submillimeter range, without relevant weakening of the irradiated electromagnetic energy over the travel path, via boundary surfaces, or via phase transitions.

According to a first embodiment of the invention, the resonance susceptibility of each individual nano-oscillator can be adapted sequentially by a targeted variation of the gradient steepness and strength to a constant stimulation frequency, with a stimulation pulse which is always at a constant frequency.

According to an alternative embodiment, the frequency of the stimulation pulse can be variably adapted sequentially in a targeted manner to the individualized resonance susceptibility of each voxel at given continuously constant gradient properties.

While the first-mentioned embodiment variant has been used successfully in spatial encoding of diagnostic magnetic resonance tomography for decades, frequency modulation technologies are used in industrial inductive metal and plastic processing, but without the use of addressing gradient fields. The technical design variant 2 is still very technically complex at the present time.

A permanent magnet, a superconducting magnet, an electromagnet, or a resistance magnet can be used to generate the $B_0$ field which creates the homogeneous orientation of the paramagnetic substance, i.e., the paramagnetic nano-oscillators, parallel or antiparallel to the magnetic field lines, and the homogenization of their field-strength-dependent susceptibility for their characteristic, resonant inductive frequency pulse. Accordingly, the apparatus can have a magnet designed in the manner above. The field strength of the (static) $B_0$ according to the invention can be ≤3 Tesla or also ≥3 Tesla. Very particularly preferably, the field strength of the $B_0$ field is >10 Tesla. Although magnetic resonance tomography with respect to the image (data) or image-based morphological monitoring of the production process is to be regarded as a gold standard, the field strength of the $B_0$ field according to the invention can be in the mT range, or greater. It is to be noted that the static, i.e., the constantly present, $B_0$ field according to the invention can be variably modulated in its spatial field orientation and/or over time in its field strength in a respectively predefined, i.e., controlled manner.

The gradient fields for spatially encoded addressing of the paramagnetic substance of the individual voxels are generated by means of gradient coils in ≤3 spatial directions. These gradient fields are briefly switched on, wherein their field strength continuously increases or drops along their respective spatial axes.

As a result, a location-specific attenuation/reinforcement of the static $B_0$ field, and thus a location encoding of the HF-susceptibility of the paramagnetic substance in three-dimensional space, are achieved by cumulative generation of magnetic micro-environments (resonance niches). In principle, the greater the increase in rise and the shorter the rise time, the better the detail resolution of the polymerization process. If a bloc polymerization (i.e., the polymerization of a plurality of voxels or a larger volume of interest) is desired, flat gradients, i.e., flat rise intensities, are advantageous.

The radio-frequency field generator (radio-frequency unit) serves to excite the paramagnetic substance or oscillators (under resonance conditions) by means of RF radiation. For this purpose, the radio-frequency unit can have an RF transmission amplifier and at least one RF transmitting coil. The RF unit can be integrated into the housing of the apparatus. Alternatively, the RF transmitting coil can be designed in the form of an RF coil that can be freely positioned relatively to the working space of the apparatus, i.e., is mobile. For example, an anatomically ergonomic surface coil and a coil that can be placed intracorporeally (e.g., endorectal coil or a catheter-mounted coil) can be considered here.

According to the invention, the radio-frequency unit can also have a plurality of RF coils in the form of array coils.

The duration of action of the RF radiation is to be selected to be “as low as reasonably achievable” (ALARA), wherein the whole-body SAR values must be respected.

According to the invention, the frequency/phase/amplitude of the RF radiation is adapted to the characteristic resonant frequency of the superparamagnetic substance and/or nanoparticles (oscillators) to be excited at a given target field strength of the superposed magnetic fields (static magnetic field+3 gradient fields) in the corresponding voxel. The aim is a maximally inductive, maximally selective excitation of the superparamagnetic substance nanoparticles (oscillators) of each, single addressed voxel under resonance conditions.

According to the invention, the intervals between the irradiations of the RF pulse (pulse periodicity) are defined as a function of the following factors: thermogenicity (characteristic power absorption+thermal efficiency) of each individual oscillator or its thermochromic sum/voxel; thermal transition threshold(s) of the polymer precursor; thermal conductivity of the polymer and/or its precursors; polymerization kinetics (material-specific/architectural-specific); polymerization pattern (see CAD); e.g., degree of resolution, thermal bridges, heat-accumulating subunits (spatial pulse density, pulse density over time); (=modulation of the energy input via temporo-spatial pulse algorithms); optionally pulse amplitude/angle of incidence with respect to the voxel to be excited.

The interval periodicity and/or pulse train length of the RF stimulation is defined primarily by the thermodynamic effects in the predefined setting, and, if necessary, limited by the maximum speed of the control unit+magnetic field gradients to switch between 2 precise 3D-voxel resonance isolations (“indirect focusing”).

According to the invention: in principle, virtually any interval between the individual pulses of the RF radiation can be present, provided that the voxel-specific or VOI-specific (volume of interest) energy input in detail or as a sum causes the desired thermal effect in the voxel/VOI; for a maximally fast voxel (or VOI) resonance isolation (target coding), a continuous RF radiation (RF pulsation) is theoretically also possible, since in principle only those oscillators oscillate thermogenically for which resonance conditions prevail; for an in vivo production of the 3D structure, a fractional pulse algorithm, for example with repetitive RF radiation cycles, is possible, which is advantageous under thermodynamic aspects and allows minimization of the global RF—and thus energy-irradiation into biological tissue.

According to the invention, the frequency of the RF radiation irradiated into the working zone can basically lie in the kilohertz to terahertz range. The frequency of the RF radiation irradiated into the working zone can in principle be between 1 KHz and 789 THz. Particularly preferably, the RF frequency is 100 Khz or 130 Khz up to 100 MHz.

The control unit of the apparatus serves the following tasks:

a. system control/monitoring
b. data management
c. CAD unit
d. image acquisition/analysis/reconstruction It goes without saying that the control unit can have application software with AI properties.

The detail resolution of the polymeric 3D structure depends in this case on: the properties of the paramagnetic substance/particles and/or (super)paramagnetic nanooscillators, such as their frequency selectivity, characteristic power absorption and thermal efficiency, where these properties can be determined experimentally for the corresponding paramagnetic substance or the nano-oscillators; the concentration and the distribution pattern of the paramagnetic substance in the polymer precursor; the steepness and speed of the dynamic gradient fields generated with the gradient coils in the three spatial directions, being voxel dimension (spatial/time) and voxel distribution (spatial/time); the radio-frequency generator with respect to the specificity and homogeneity of the inductive RF radiation, the position, the width, the amplitude and angle of incidence relative to the main magnetic field; and the spatial and temporal distribution of the RF radiation (RF pulses) (pulse algorithm); the 3D heat pattern; polymerization kinetics (e.g., transition thresholds); material-specific thermodynamic phenomena; architectural thermodynamic phenomena.

A decreasing detail resolution of the method from one procedural level to the next must also be considered: constructive resolution (CAD); electromagnetic (inductive) resolution; thermal resolution; temporal resolution; polymeric resolution; structural resolution; diagnostic resolution (imaging, e.g., MRT); post-processing resolution (dependent on the method).

In clinical use, in this context, the transition zone of the polymer composite to the surrounding tissue offers particular challenges, since significant thermal losses occur here due to tissue-specific heat dissipation, absorption and perfusion phenomena, and possibly also movement artifacts. Relative and absolute thermal tolerance thresholds of biological tissues must also be respected.

A limiting factor of the resolution of the diagnostic MRI will ultimately always be the signal-to-noise ratio, i.e., the number of excited protons and/or the sum of their acquirable provoked echoes per volume unit relative to the ambient noise. This is because the stimulating RF pulses of the MRI-Scanner—apart from pre-saturation pulses, always excite all protons of a layer or in the entire pre-selected 3D examination volume, and the precise spatial encoding takes place not until the readout step. In contrast, according to the invention, ideally only those oscillators are specifically excited by preselected (resonance-isolated or resonance vulnerable) voxels of the polymer precursor which are to be cured as part of the 3D structure according to the construction plan. The gradient fields are thus activated primarily prospectively according to the invention, whereas conventional MRI sequences initially define layer orientation and thickness within the examination volume by means of only 1 gradient field (usually z-axis), and only after the RF pulse, at the time of the echo readout, are further gradient echoes (usually x-, y-axis) added for the retrospective spatial encoding. While repetitive stimulation cycles are indispensable for the analysis of the nuclear magnetic resonance echoes by means of Fourier transform, and lead to an undesired increase in the energy absorption doses, MRiP does moderate the energy dose in a targeted manner applying temporo-spatial impulse-algorithms.

In general, the resonant frequency of the oscillators in the manufacturing process should deliberately be selected to be not equal to the proton resonant frequency in order to avoid heterotopic polymerizations by MRT control imaging. An exception would be certain preformed "squids", e.g., 3D structures in the form of thermoresponsive stents/cages/cava filters, coils/occluders, heart valves, vessel endoprostheses, thermoresponsive bone cement, or tissue adhesives.

Further developments of the method could also benefit from a combination of different oscillator types with corresponding frequency variation. After all high frequencies are known to lead to a steeper temperature rise in the immediate vicinity of the oscillator, but low frequencies lead to a gentle, homogeneous, global heating of the further environment. However, corresponding effects could also result by varying the angle of incidence in the monofrequency pulse setting.

While morphological features of <200 μm cannot be reproduced sufficiently in clinical MRI routine diagnostics to date, MRiP respectively the apparatus according to the invention/the system according to the invention is able to additively generate structures (e.g., pores) orders of magnitude smaller, on an order of magnitude relevant for cell navigation, cell control, and histogenetic determination, for spatial and temporal control of tissue regeneration.

The manufacturing result of the MRiP can also be further improved by a repetitive real-time image acquisition, for example on the basis of robust MRI-sequences, or alternatively also by other imaging devices/methods of comparable spatial resolution (e. g., surface-laser-scanners, DVT, etc.).

The method according to the invention can comprise the further step of postprocessing of the 3D structure after the printing of the 3D structure. The 3D structure can thus be kept as a whole at a predetermined temperature over a defined period of time and/or can be cooled in total in a predefined manner, in particular stepwise. In the first case, an optionally required "post-maturation" of the 3D polymer structure, i.e., complete polymerization of the entire 3D structure, in particular, after removal of excess prepolymer, can be achieved. A heat input required for this purpose can be achieved, for example, without previous spatial encoding of individual voxels, by irradiating the 3D structure with RF radiation or by applying infrared radiation and/or supplying hot air.

For cooling the entire 3D structure, the aforementioned active heat input into the 3D structure, e. g., stepwise, can be reduced over time, or the 3D structure can be cooled in a controlled manner by active heat removal, for example by application of a cooling medium (e. g., air or water). Undesired stress cracks and the like in the 3D structure can thereby be prevented.

Use of the Apparatus/Polymer Precursor/System:

The above-explained apparatus or the system or the polymer precursor can be used universally in the fields of technology and medicine. Thus, they can be used or employed in particular, for producing a medical implant, in particular bone replacement, a supporting framework for an organ or tissue, or a vascular prosthesis.

Specifically:

Use in human, dental, and animal medicine: plastic radiology: stabilization of tissue/generation of placeholders; reconstruction of tissue/replacement of tissue; adaptation/anchoring/embolization; augmentation/contouring/enhancement; and compartmentalization/encapsulation of pathological processes or so/masking.

Subtle initial damage can be contained and/or remedied at the earliest possible point in time, and vulnerable individual tissues that are particularly endangered can be a priori enhanced, with the potential for preventing wear, e.g., in performance sports, and thus including but not limited work-related early invalidism, resulting in an enormous health-economic and economic benefit.

Reparative and Reconstructive Radiology:

In addition to the specific replacement of connective and supporting tissues (cartilage, bones, tendons, ligaments), the apparatus/polymer precursor/system is suitable both for plastic reconstruction, functional and aesthetic shaping, and shape correction, as well as for diffuse tissue stabilization for primary and secondary tissue tone losses.

The polymer precursor and/or the 3D structure produced therefrom can furthermore be used as a binder in fracture zones and arthrodesis, as an adhesive for the treatment of acute wounds and as a bioactive protector, as a mesh replacement in hernioplasty, and as a placeholder, guide structure, and support material for cellular structures and/or acellular additives and active agents. Furthermore, the invention allows the synthesis, anastomosis, stabilization, adaptation, and occlusion of cavities in vivo, including valve, sphincter and shunt systems, largely independently of their dimensions, configuration and location. For a large number of hitherto unsatisfactory treatments of chronic diseases such as PAOD, lymphedema, and chronic venous insufficiency, this promises individualized curative strategies for the first time—and should also significantly improve the outcome of classic (microvascular) grafts and limb-replants.

The invention can also be used to optimize the biomechanical coupling of prostheses and, far in the future, even to reconstruct and link neural conductive structures in a targeted manner.

In particular, however, the invention allows the interface to be authentically created in situ between a wide variety of tissues and materials in order to effect optimal structure integrity, force direction, and force transmission. These can be precisely modulated at any time and can be repeatedly adapted to different individual load profiles and complex movement patterns of each patient. This takes place by image-controlled real-time modulation of the process parameters of the apparatus, and also by non-invasive and invasive post-processing.

The invention can be used for gentler and at the same time more efficient anchoring of an implant, in particular a joint endoprosthesis. With advancing wear, the apparatus and also the polymer precursor can be used in vivo to recoat the endoprosthesis.

The invention can also be used to generate a large or full-surface bioartificial cartilage replacement in situ.

Captive Radiology:

The apparatus/system/the polymer precursor can be used for risk management and limiting complications of tumorous and inflammatory diseases by means of the 3D structure by closing off afflicted anatomical compartments. As a result, it is possible to treat the pathological processes inside an isolated, "neoanatomic" space, for example chemo- or immunotherapeutically, radiooncologically or thermally treated, or confine them in a palliative manner.

Since the metastasis probability increases with increasing tumor surface, even an incomplete sheathing of tumors by means of the 3D structure generated in vivo can already be associated with a relative prognosis benefit. The artificial polymeric sheathing can also serve as a guide structure for a biopsy, as an orientation aid during the tumor resection, as a solidified safety margin, and quite generally as a spacer or as a protective shield for vulnerable structures.

Manufactive Radiology:

The apparatus/system and/or the polymer precursor can be used for manufacturing 3D structures in the form of guide elements, anatomical (e. g., electroconductive) guidewires and polymeric 3D rail networks, as well as bioartificial sensor technologies and conductor systems. As a result, the looming automation of medical therapy and diagnostics for example by intra-corporeal (partially) autonomous miniature robots, soft robots or, in particular, intracorporeal, portable electronic devices, can be further advanced.

It should be noted that the apparatus/system and/or the polymer precursor according to the invention can be used with robotic assistance, for telemetric remote-control intervention (remote manufacturing), in particular, using CAD construction libraries, in order to meet care needs in remote locations—e.g., ISS—or in crisis situations, and maintain critical infrastructures.

Depending on the site of the 3D structure to be produced in vivo, the access route, rheological properties, or patient variables, the polymer template can be introduced directly into the body or into the target location via cannulas, catheters, endoscopes, or other expedient instruments, either as an infusion, injection, or instillate.

A possible variant can be the ballooning-technique, i.e., the provision of at least one single-lumen or multi-lumen balloon expander for local tissue pre-stretching, i.e., deployed by catheter, whereupon the magnetic resonance induction polymerization can take place optionally with direct tissue contact or primarily in the balloon lumen, for example in the case of substance incompatibilities, or the necessity of an accompanying chemical surface hardening of the product or its forced thermal postprocessing or cooling by means of perfusion systems.

According to the invention, voxels in the polymer precursor can be defined for the production process, with voxels each having a uniform size or which at least partially differ from one another in terms of their size. By defining differently sized voxels or VOIs (volumes of interest), 3D structures having a complex geometry can be generated more rapidly.

During the manufacturing process, at least a portion of the voxels defined on the basis of the CAD/CAM data can be modified in terms of their spatial position in the working zone, size, and/or their geometry for the manufacturing process on the basis of image data acquired in particular by magnetic resonance tomography. The manufacturing tolerance of the 3D structure can thereby be further improved.

According to a development of the invention, the manufacturing process is interrupted, preferably in intervals, in order to capture image data from the working zone, in particular from the 3D structure already produced, or the volume of the polymer precursor adjacent to the 3D structure. The image data can in particular be acquired depending on the CAD/CAM data of the 3D structure to be produced.

The image data are preferably compared with the CAD data and, when a deviation of the already (partially) manufactured 3D structure is detected, the CAD/CAM data for generating the remaining 3D structure are modified on the basis of the image data. An extraordinarily tight manufacturing tolerance of the 3D structure can be realized in this way.

According to the invention, the 3D structure can be produced partially or completely within a living being in order to be available as an implant after it has been removed, or in order to fulfill its function in situ.

According to the invention, the 3D structure can be a support framework for tissue, an organ, in particular a bone, a kidney, a liver, a cartilage replacement, a bone replacement or a vessel portion.

Further advantages of the invention can be found in the description and the drawings. The embodiments shown and described are not to be understood as an exhaustive list, but, rather, have an exemplary character for the description of the invention.

DETAILED DESCRIPTION OF EMBODIMENTS OF THE INVENTION

Figure 1:
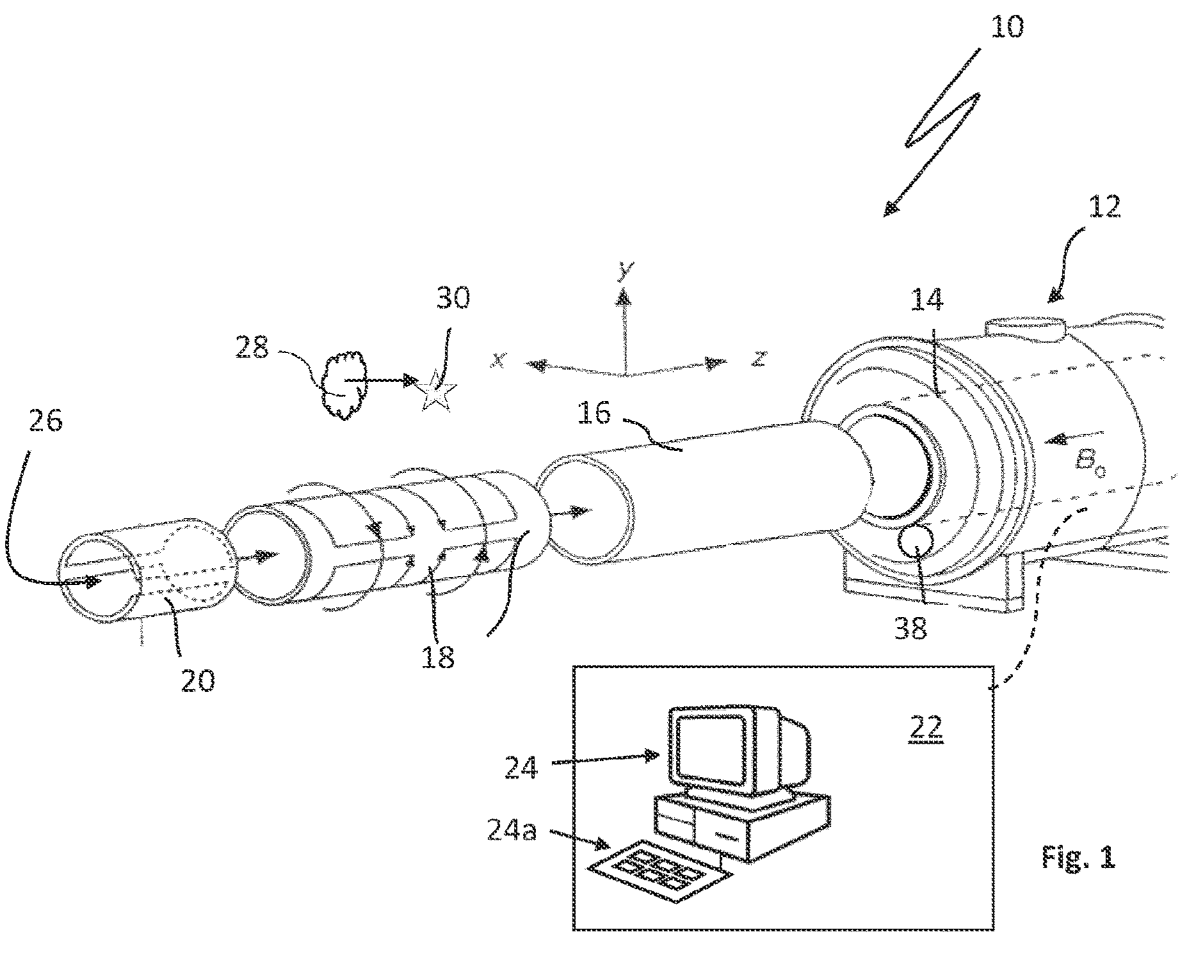
FIG. 1 is the schematic structure of a system according to the invention, having an apparatus and having a polymer precursor that can be arranged in the working zone of the apparatus.

FIG. 1 is a system 10 having an apparatus 12 which has a magnetic field generator 14 for generating a static magnetic field $B_0$, optional shim coils 16 and gradient coils 18, an RF field generator 20, a control unit 22 with a computer system 24 and an input and operating console 24*a*, and a working zone 26. A polymer precursor 28 can be arranged in the working zone 26 as the starting material for the 3D structure 30 to be produced with the apparatus 12.

The magnetic field generator 14 serves to generate a homogeneous static magnetic field $B_0$ (hereinafter referred to as the $B_0$ field) in the working zone 26. The field strength of the $B_0$ field is greater than the Earth's magnetic field by orders of magnitude. It is to be noted that the static $B_0$ field can be variably modifiable in terms of its field orientation and/or over time with regard to its field strength. The magnetic field generator 14 can, for example, comprise a permanent magnet or a superconducting magnet. This homogeneous $B_0$ field can be modified in a targeted manner by the gradient coils 18. The gradient coils 18 are preferably located on the circumference of the working zone 26. With these gradient coils 18, continuously increasing or diminishing magnetic fields, so-called gradient fields, can be superimposed on the static $B_0$ field in all three spatial directions x, y, z.

Figure 2:
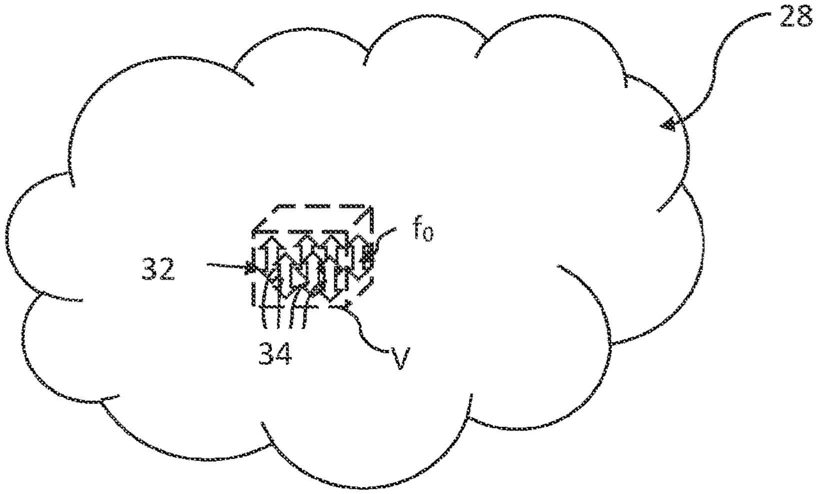
FIG. 2 is the polymer precursor with the paramagnetic substance in a selected voxel of the polymer precursor.

The polymer precursor 28 comprises, according to the schematic representation of a voxel V of the polymer precursor in FIG. 2, a paramagnetic substance 32 which is preferably arranged homogeneously distributed in the polymer precursor 28. The paramagnetic substance 32 is preferably formed by superparamagnetic nanoparticulate metal particles 34 (nanooscillators) which are suspended in the polymer precursor 28. The metal particles 34 can in particular, consist of nanoparticulate magnetite ($Fe_3O_4$) or a silver halide ($Ag_nX_n$). One milliliter of the polymer precursor 28 preferably contains more than 1000, preferably more than 10,000, and up to $10^{17}$ metal particles 34.

In the static $B_0$ field all metal particles 34 orient their rotational moments parallel or antiparallel to the magnetic field lines of the $B_0$ field. This is accompanied by a synchronization of their resonant frequency sensitivity for irradiated RF radiation or RF pulses. In addition to the material, polarity, and geometry and size of the metal particles 34, the resonant frequency susceptibility depends on the field strength of the $B_0$ field. For each field strength of the $B_0$ field therefore, essentially only one single specific frequency of the electromagnetic RF radiation exists which maximally stimulates all of the metal particles configurated in the same way as oscillators: the so-called resonant frequency.

In simple (theoretical) systems without attenuation, the resonant frequency is equal to the undamped natural frequency (characteristic frequency) $f_0$ of the paramagnetic metal particles 34. In attenuated systems, the frequency at which the maximum amplitude occurs is always lower than the unattenuated natural frequency.

Under resonance conditions, all metal particles 34 excitable by the RF radiation thus have a maximum energy absorption susceptibility with regard to the specific RF alternating field. This results in a significantly increased oscillatory movement of the metal particles 34. These oscillatory movements are converted (at the molecular level) into thermal energy due to resistance and friction effects with a minimum spatial coupling distance. The metal particles can thus be referred to as nano-oscillators.

The dynamic gradient fields (B1, B2, B3; not shown in the drawing) of the apparatus 12 serve in a manner corresponding to that of nuclear magnetic resonance tomography for slice selection and location encoding in at least 3 spatial directions—i.e., functionally for "indirect focusing" of the RF radiation irradiated into the working zone by means of the RF field generator 20. The gradient fields are characterized by a continuous increase or decrease in the corresponding magnetic field strength along their characteristic axes x, y, z, relative to the B0 field. At this point, reference is made to the gradient fields familiar to the person skilled in the art of nuclear magnetic resonance tomography. An introduced gradient field in the x-axis thus is superimposed on the previously homogeneous permanent static $B_0$ field, and thus leads to a linear increase or decrease of the total static field strength along the x-axis. The same applies to each introduced gradient field along the y-axis and z-axis. The consequence of this is that each metal particle or each spatial volume or voxel of the polymer precursor 28 has in three-dimensional space its own individual electromagnetic niche inherent to it in the intersection of the at least 3 gradient fields.

Thus, if the magnetic micro-environment of each oscillator or each voxel differs linearly from the magnetic micro-environment of its neighbor oscillator or adjacent voxel (neighboring voxel) in all three spatial directions, then each nanoparticle and/or the nanoparticles of each individual voxel has/have its own, individual resonant frequency, and can be individually addressed in isolation, and selectively excited by an undirected electromagnetic RF field. In this case, the respective steepness of the x, y, z gradient fields defines the edge lengths of the voxels in all 3 spatial directions x, y, z, optimally by a simultaneous total superposition of their local field strength—or alternatively, sequentially, e.g., using the inverse Fourier transform.

The control unit 22 of the apparatus 12 is configured to control the RF field generator 20 in such a way that RF radiation with a field frequency tuned to the resonant frequency of the metal particles/oscillators is irradiated into the working zone 26 in order to locally heat and polymerize the polymer precursor 28 in the afore spatially-encoded voxel V or in the afore spatially-encoded contiguous volume unit of the polymer precursor "en bloc".

The typical field frequency of the RF radiation for oscillation excitation of the paramagnetic substance is between 1 KHz and 789 THz, in particular between 100 KHz or 130 KHz and 789 THz.

The control unit 22 of the apparatus 12 preferably has an operating mode which serves to obtain image data (e.g., magnetic resonance tomography image data) from the working zone 26 and/or from the polymer precursor 28 and/or the already-polymerized 3D structure 30. The control unit 22, in particular, the computer system 24, serves to control all operating processes of the apparatus 12 on the basis of specified CAD/CAM data. Furthermore, the control unit 22 is preferably configured to evaluate the image data. The control unit 22 can thus in particular be configured to compare the CAD/CAM data with the previously obtained image data and, when a discrepancy which is greater than a predefined permissible maximum deviation is detected, to continue the further manufacturing process on the basis of the image data. Here, the control unit can in particular be configured (programmed) to modify the CAD/CAM data for the remaining 3D structure to be generated. In this way, the 3D structure can be manufactured with particularly tight tolerances.

In the case of in vivo generation (manufacturing) of the 3D structure 30, information regarding the anatomical structures adjacent to or interacting with the 3D structure can furthermore be taken into account in real time in the manufacturing process. Here, the use of artificial intelligence or a software application with AI capability can be advantageous, especially since systematic deviations recognized in the manufacturing process, possibly depending on the polymer precursor used, the paramagnetic substance, the environmental variables, etc., can be taken into account and prospectively incorporated in the creation/modification of the CAD/CAM and data for the relevant 3D structure and/or the production process.

Figure 3:
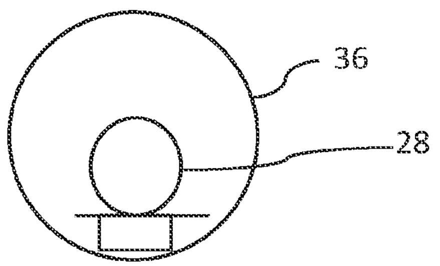
FIG. 3 is a housing within which the polymer precursor can be arranged during the 3D manufacturing process.

According to FIG. 3, the working zone 26 of the apparatus can be encompassed by a preferably gas-tight housing 36. The housing 36 can be formed, for example, from plastic or glass or another material which is non-shielding against RF fields or magnetic fields. The housing can be formed, for example, by a plastic film in which the polymer precursor 28 is arranged.

The working zone of the apparatus 12 can be assigned a pump 38 (FIG. 1) by means of which the atmosphere in the housing 36 can be evacuated or substantially evacuated and/or via which the working zone within the housing 36 can be filled with a fluid, in particular a working atmosphere A, specified for the production process. In this way, for example, undesired oxidative processes of the polymer precursor 28 by oxygen contained in the working atmosphere A can be counteracted.

The apparatus 12 can in particular be formed by a modified MRT device, the control unit 22 of which is adapted to the production of the 3D structure in the manner explained above.

The polymer precursor 28 can have identical or different monomers or polymers (in particular, also dimers, oligomers). Furthermore, the polymer precursor 28 can comprise fibers and/or one or more other additives, as explained at the outset. Purely by way of example, these may be additives from the group of dyes, antibacterial substances, antibiotics, or growth factors.

Depending on the mechanical, electrical or biological requirements demanded from the 3D structure, the polymer precursor 28 can have a viscosity of approx. $10^2$ mPa·s to $10^5$ m Pa·s, or greater. If the 3D structure 30 will be used, for example, as an implant in a human/animal, the polymer precursor 28, in the non-polymerized state, is preferably a substance that can be broken down in a non-toxic manner, and preferably can be eliminated by the body's own enzymes, and/or can be eliminated by the human/animal body by natural processes.

The apparatus 12 can be used universally. For example, medical implants, in particular bone replacement, support structures for tissue/organs, or vascular prostheses, can thus be produced. This can take place in vitro or also directly in vivo.

Figure 4:
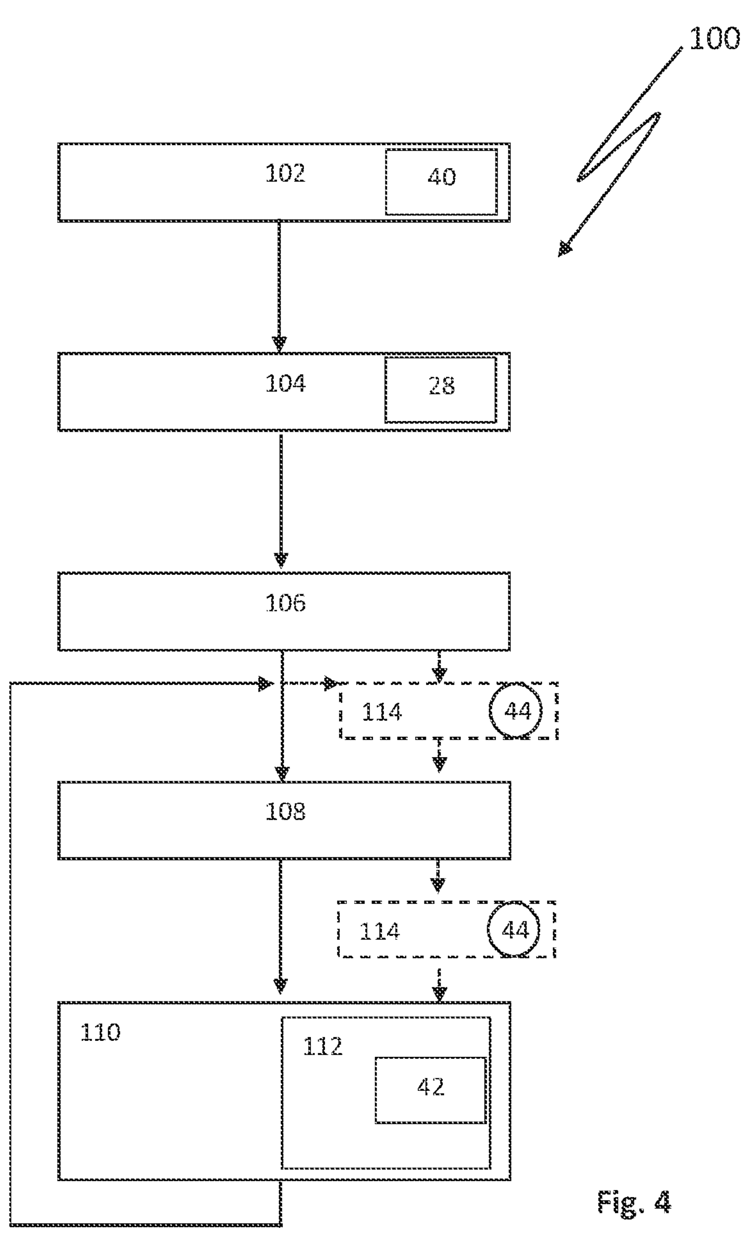
FIG. 4 is a block diagram of the method according to the invention for generating a 3D structure, with individual method steps.

Below, the method 100 for generating a 3D structure is explained in more detail with additional reference to the block diagram shown in FIG. 4.

The method 100 for generating the 3D structure 30 (FIG. 1) necessarily presupposes the use of the system 10 described above in the context of FIGS. 1 to 4 with the apparatus 12 and with the polymer precursor 28 according to the invention, and comprises the following steps:

a. defining 102 CAD/CAM data 40 for the 3D structure 30 to be produced;
b. providing 104 a polymer precursor 28 having a paramagnetic substance 32 distributed as homogeneously as possible therein;
c. introducing 106 the polymer precursor 28 into the working zone of the apparatus;
d. spatially encoding 108 a voxel V within the polymer precursor 28 according to the CAD/CAM data by applying magnetic gradient fields;
e. polymerizing 110 the polymer precursor 28 in the at least one spatially encoded voxel V by irradiating 112 RF radiation 42 by means of which the paramagnetic substance 32 is excited to oscillations in the corresponding voxel V; and
f. subsequently sequentially spatially encoding 108 of further voxels V, preferably spatially adjacent to one another, in the polymer precursor 28 as a function of the CAD/CAM data 40, and polymerizing 110 the corresponding further spatially encoded voxels V by irradiation 112 of RF radiation 42 by means of which the paramagnetic substance 32 is excited to oscillations in the corresponding further voxel V.

The frequency of the RF radiation 42, i.e., the applied RF field, is preferably tuned to the corresponding resonant frequency $f_0$ of the paramagnetic substance 32 or the metal particles 34 of the polymer precursor 28 to be excited with the RF radiation. The resonant frequency $f_0$ of the corresponding paramagnetic substance 32 can be determined experimentally.

It should be noted that the voxels V can each have a uniform size or can at least partially differ from one another in terms of their size.

According to a development of the invention, in an optional step 114, image data 44 of the non-polymerized and/or polymerized polymer precursor 28 is obtained, in particular, by magnetic resonance tomography or by way of an alternative imaging method, for the polymer precursor 28. This step can, in particular, take place before (in particular during step c) and/or after the step d) indicated above, in particular after step e), and preferably as a function of the CAD/CAM data 40.

In an optional step, the image data 44 can be compared with the CAD/CAM data 40, and the CAD/CAM data 40 for the 3D structure 30 can be modified on the basis of the image data to generate the remaining 3D structure 30, if a maximum deviation of the already generated 3D structure 30 is exceeded. In this way, the 3D structure 30 can be generated with particularly tight tolerances.

For medical indications, the 3D structure 30 can be printed completely in a first living being (not shown in the drawing), i.e., in vivo, in order to be available as an implant for another living being (not shown) after removal thereof.

By means of the method 100 according to the invention, any 3D structures, for example machine parts, support scaffolds for cells, tissues, organs, etc., can be generated as described at the outset.

What is claimed is:

1. An apparatus configured for generating a 3D structure, comprising:

a magnetic field generator configured for generating a static magnetic field $B_0$ in a working zone of the apparatus, in which a polymer precursor comprising at least one paramagnetic substance can be arranged;

gradient coils configured for generating magnetic gradient fields in all three spatial directions x, y, z, by means of which the paramagnetic substance can be spatially encoded in a defined voxel V of the polymer precursor;

a radio-frequency field generator configured for irradiating RF radiation into the working zone; and a control unit which is configured to control the RF field generator where the spatially encoded paramagnetic substance in the voxel V can be excited by means of a field frequency of the RF radiation tuned to the paramagnetic substance configured to trigger polymerization of the polymer precursor in the defined voxel V.

2. The apparatus according to claim 1, wherein the field frequency is between 1 KHz and 789 THz.

3. The apparatus according to claim 1, wherein the control unit has an operating mode configured for obtaining image data from the working zone, being magnetic resonance tomography image data.

4. The apparatus according to claim 3, wherein the control device is configured to compare the image data with CAD/CAM data for the 3D structure and, if deviations of the partially-generated 3D structure from the CAD/CAM data are detected, being geometric deviations, to take into account the image data and/or the deviations during further printing of the 3D structure.

5. The apparatus according to claim 4, wherein the control unit is configured to change the CAD/CAM data on the basis of the image data.

6. The apparatus according to claim 1, wherein the working zone is arranged within a housing.

7. The apparatus according to claim 6, wherein the housing comprises a plastic film or a glass.

8. The apparatus according to claim 1, wherein the apparatus has a pump by means of which ambient atmosphere in the working zone can be evacuated or substantially evacuated and/or via which the working zone can be filled with a working atmosphere A and/or a fluid that is prespecified for a production process.

9. The apparatus according to claim 1, wherein the apparatus further comprises a temperature control device configured for controlling a temperature of the working zone.

10. The apparatus according to claim 1, wherein the apparatus further comprises an MRT device or a different imaging unit.

11. The apparatus according to claim 1, wherein the field frequency is between 100 KHz or 130 KHz and 789 THz.

12. A system for generating the 3D structure, comprising the apparatus according to claim 1 and the polymer precursor with the at least one paramagnetic substance.

13. The system according to claim 12, wherein the paramagnetic substance comprises metal particles or metal organyls.

14. The system according to claim 13, wherein the metal particles comprise nanoparticulate magnetite particles or nanoparticulate iron particles.

15. The system according to claim 14, wherein the metal particles are present in a concentration of >10,000 particles per milliliter of the polymer precursor.

16. The system according to claim 13, wherein the metal particles are present in a concentration of >1000 particles per milliliter of the polymer precursor.

17. The system according to claim 13, wherein at least a portion of the metal particles differ from one another by having a different size or shape.

18. The system according to claim 13, wherein the metal particles are each coated with titanium.

19. The system according to claim 12, wherein the polymer precursor comprises at least two different monomers or different polymers.

20. The system according to claim 12, wherein the polymer precursor comprises polysaccharides, and/or methacrylic acid and/or polylactides and/or PLA derivatives and/or ECM derivatives and/or artificial polymers and/or bioartificial polymers.

21. The system according to claim 12, wherein the polymer precursor comprises one or more additives selected from the group of fibers, dyes, antibacterial substances, growth factors, nanoparticles/tubes, mineral fillers, metallic materials, glycosaminoglycans, MMC substances, polypeptide motifs, promoters, terminators, inhibitors, catalysts, sensitizers, and/or immunomodulators.

22. The system according to claim 12, wherein the polymer precursor has a viscosity of 102 mPa·s to 106 mPa·s.

23. The system according to claim 12, wherein the polymer precursor can be broken down and/or removed in a non-polymerized state in a human and/or animal body by endogenous enzymes.

24. A method, comprising forming the 3D structure by the system according to claim 12 in a form of a machine element or a medical implant.

25. The method according to claim 24, wherein the forming of the 3D structure takes place at least partially or completely in vivo.

26. A method for producing the 3D structure by means of the system according to claim 11, comprising the following steps:

a) defining CAD/CAM data for the 3D structure to be produced;

b) providing the polymer precursor comprising the paramagnetic substance;

c) introducing the polymer precursor into the working zone of the apparatus;

d) spatially encoding the voxel V within the polymer precursor as a function of the CAD/CAM data by applying the magnetic gradient fields;

e) polymerizing the polymer precursor in the at least one spatially encoded voxel V by irradiating the RF radiation by means of which the paramagnetic substance is excited to oscillations in the corresponding voxel V; and f) subsequently sequentially spatially encoding further voxels V in the polymer precursor as the function of the CAD/CAM data, and polymerizing the corresponding further spatially encoded voxels V by irradiating the RF radiation by means of which the paramagnetic substance is excited to oscillations in the corresponding further voxels V.

27. The method according to claim 26, wherein the field frequency of the RF radiation is selected depending on the known resonant frequency $f_0$ of the paramagnetic substance of the polymer precursor to be excited with the RF radiation.

28. The method according to claim 26, wherein the voxels V are each defined with a uniform volume size, or in that the voxels V are at least partially defined with a different volume size.

29. The method according to claim 26, wherein image data are obtained from the polymer precursor and/or the partially generated 3D structure, being magnetic resonance tomography data, and a further manufacturing process takes place taking into account the magnetic resonance tomography data.

30. The method according to claim 26, wherein the method further comprises comparing image data with the CAD/CAM data, and changing the CAD/CAM data for the 3D structure if a maximum deviation of the image data from the CAD/CAM data is exceeded, on the basis of the image data.

31. The method according to claim 26, wherein the 3D structure is in a form of a machine element or an implant.

32. The method according to claim 26, wherein the 3D structure is produced completely in vivo in a first living being in order to be available as an implant for a second living being after the 3D structure is removed from the first living being.

* * * * *